United States Patent [19]

Muskopf et al.

[11] Patent Number: 5,140,079

[45] Date of Patent: Aug. 18, 1992

[54] LATENT, CURABLE, CATALYZED MIXTURES OF EPOXY-CONTAINING AND PHENOLIC-HYDROXYL-CONTAINING COMPOUNDS CONTAINING COMPOUNDS OR COMPLEXES FORMED FROM CONTACTING ORGANIC PHOSPHINES OR ARSINES WITH WEAK NUCLEOPHILIC ACIDS

[75] Inventors: John W. Muskopf, Lake Jackson; Louis L. Walker, Clute; James L. Bertram, Lake Jackson, all of Tex.

[73] Assignee: The Dow Chemical Company, Midland, Mich.

[21] Appl. No.: 685,332

[22] Filed: Apr. 15, 1991

Related U.S. Application Data

[63] Continuation-in-part of Ser. No. 477,410, Feb. 6, 1990, abandoned.

[51] Int. Cl.$^5$ .............................................. C08G 59/68
[52] U.S. Cl. ................................. 525/482; 525/485; 525/506; 525/507; 525/523; 525/534; 528/88; 528/89; 528/104; 528/92
[58] Field of Search ................ 525/482, 485, 506, 507, 525/534, 523; 528/88, 89, 104, 92

[56] References Cited

U.S. PATENT DOCUMENTS

| | | | |
|---|---|---|---|
| 3,947,395 | 3/1976 | Ogata et al. | 528/89 |
| 4,451,450 | 5/1984 | Subramanyam | 528/89 |
| 4,477,645 | 10/1984 | Doorakian et al. | 528/89 |
| 4,512,967 | 4/1985 | Linder | 528/89 |
| 4,540,823 | 9/1985 | Doorakian et al. | 528/89 |
| 4,594,291 | 6/1986 | Bertram et al. | 528/97 |
| 4,634,757 | 1/1987 | Marshall | 528/89 |
| 4,692,504 | 9/1987 | Frank | 528/89 |
| 4,725,652 | 2/1988 | Bertram et al. | 528/91 |
| 4,775,734 | 10/1988 | Goel | 528/89 |
| 4,925,901 | 5/1990 | Bertram et al. | 528/89 |

FOREIGN PATENT DOCUMENTS 58-138729  8/1983  Japan .
0963058  7/1964  United Kingdom .

OTHER PUBLICATIONS

"Proposed Mechanism for Curing of Epoxy Resins with Amine-Lewis Acid Complexes or Salts", James J. Harris and Samuel C. Temin, *J. App. Polym. Sci.*, vol. 10, pp. 523-534 (1966).

*Primary Examiner*—John C. Bleutge
*Assistant Examiner*—Frederick Krass

[57] ABSTRACT

The products resulting from contacting an organic phosphine or arsine with an inorganic acid having a weak nucleophilic anion provide for relatively stable compositions when admixed with a compound containing an average of more than one vicinal epoxide group per molecule and which optionally contains a compound containing an average of more than one phenolic hydroxyl group per molecule.

12 Claims, No Drawings

LATENT, CURABLE, CATALYZED MIXTURES OF EPOXY-CONTAINING AND PHENOLIC-HYDROXYL-CONTAINING COMPOUNDS CONTAINING COMPOUNDS OR COMPLEXES FORMED FROM CONTACTING ORGANIC PHOSPHINES OR ARSINES WITH WEAK NUCLEOPHILIC ACIDS

CROSS-REFERENCE TO RELATED APPLICATIONS

This application is a continuation-in-part of application Ser. No. 07/477,410 filed Feb. 6, 1990, now abandoned, which is incorporated herein by reference in its entirety.

FIELD OF THE INVENTION

The present invention concerns latent, curable, catalyzed mixtures of epoxy-containing compounds and aromatic hydroxyl-containing compounds. The present invention also concerns latent catalysts and epoxy resin compositions containing them.

BACKGROUND OF THE INVENTION

Epoxy resins have been precatalyzed with phosphonium and other compounds to provide latent compositions which form advanced, higher molecular weight epoxy resins when admixed with an aromatic hydroxyl-containing compound as disclosed by Perry in U.S. Pat. No. 3,948,855 and Can. 893,191; by Dante et al. in U.S. Pat. No. 3,477,990; by Mueller et al. in U.S. Pat. No. 3,547,881; by Tyler, Jr. et al. in U.S. Pat. No. 4,366,295; and by Cragar in Can. 858,648.

While compositions containing these catalysts and an epoxy resin are somewhat stable, such compositions which also contain an aromatic hydroxyl-containing compound are lacking in stability.

SUMMARY OF THE INVENTION

One aspect of the present invention pertains to new latent catalysts for epoxy resins which are the adducts, complexes or compounds resulting from (1) contacting (a) at least one organic phosphine or organic arsine with (b) an inorganic acid having a weak-nucleophilic anion or a combination of such acids; or (2) contacting (a) at least one adduct of an acid having a relatively strong-nucleophilic anion and an organic phosphine or organic arsine with (b) an inorganic acid or metal salt of an inorganic acid, said acid having a weak-nucleophilic anion or a combination of such acids or metal salts; wherein components (a) and (b) are contacted in quantities which provide a molar ratio of component (a) to component (b) of from about 0.6:1 to about 1.4:1; with the proviso that when component (1-a) is a phosphine, it is a phosphine other than triphenyl phosphine.

Another aspect of the present invention pertains to new latent catalysts for epoxy resins which are adducts, complexes or compounds represented by the following Formulas I or II.

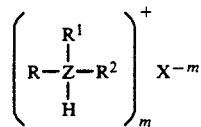

Formula I.

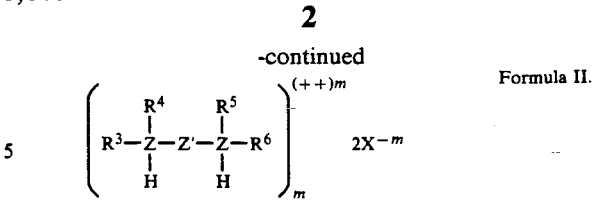

wherein each R, $R^1$, $R^2$, $R^3$, $R^4$, $R^5$ and $R^6$ is independently a hydrocarbyl group having from 1 to about 18 carbon atoms or two of such R, $R^1$, or $R^2$ groups or $R^3$ and $R^4$ groups or $R^5$ and $R^6$ groups can combine to form a heterocyclic ring; each X is the anion portion of a relatively weak nucleophilic acid; Z is P or As; Z' is a divalent hydrocarbyl group having from 1 to about 10 carbon atoms; and m has a value equal to the valence of the anion X; and with the proviso that at least one such R, $R^1$ or $R^2$ group in Formula I is a group other than a phenyl group and with the proviso that at least one such $R^3$, $R^4$, $R^5$ or $R^6$ group in Formula II is a group other than methyl when Z' is a —$CH_2$—$CH_2$— group.

Another aspect of the present invention pertains to compositions comprising (A) at least one compound containing an average of more than one epoxide group per molecule; and (B) at least one of (1) the product resulting from contacting (a) at least one organic phosphine or arsine with (b) an inorganic acid having a weak-nucleophilic anion or a combination of such acids; or (2) the product resulting from contacting (a) at least one adduct of an acid having a relatively strong-nucleophilic anion and an organic phosphine or arsine compound with (b) an inorganic acid or metal salt of an inorganic acid, said acid having a weak-nucleophilic anion or a combination of such acids or metal salts; wherein (i) components (a) and (b) are contacted in quantities which permit the composition to satisfy the viscosity requirements of the composition after storage at 50° C. for 14 days; and (ii) a mixture of components (A), and (B), when dissolved in 20 to 40 percent by weight of a suitable solvent or solvent mixture has a viscosity measured at 25° C. of 75% or less, preferably 10% or less, more preferably 1% or less, than the viscosity of a like composition except that the catalyst consists only of component (a), said viscosity being determined after storage for 14 days at 50° C.

Another aspect of the present invention pertains to compositions comprising (A) at least one compound containing an average of more than one epoxide group per molecule; (B) at least one compound containing an average of more than one aromatic hydroxyl group per molecule; and (C) at least one catalyst selected from the group consisting of (1) the product resulting from contacting (a) at least one organic phosphine or arsine with (b) an inorganic acid having a weak-nucleophilic anion or a combination of such acids; and (2) the product resulting from contacting (a) at least one adduct of an acid having a relatively strong-nucleophilic anion and an organic phosphine or arsine compound with (b) an inorganic acid or metal salt of an inorganic acid, said acid having a weak-nucleophilic anion or a combination of such acids or metal salts; wherein (i) components (a) and (b) are contacted in quantities which permit the composition to satisfy the viscosity requirements of the composition after storage at 50° C. for 14 days; (ii) components (A) and (B) are present in quantities which provide a ratio of aromatic hydroxyl groups to epoxide group of from about 0.05:1 to about 20:1; and (iii) a mixture of components (A), (B), and (C), when dissolved in 20 to 40 percent by weight of a suitable solvent or solvent mixture, has a viscosity measured at 25° C. of 75% or less, preferably 10% or less, more preferably 1% or less, than the viscosity of a like composition except that the catalyst consists only of component (a), said viscosity being determined after storage for 14 days at 50° C.

The term weak-nucleophilic as employed herein means that the compound has a nucleophilicity value "n" of from about zero to less than about 2.5 as described by C. G. Swain and C. B. Scott in J. Am. Chem. Soc., Vol. 75, p. 141 (1953) which is incorporated herein by reference.

The term relatively strong-nucleophilic as employed herein means that the material has a nucleophilicity value "n" of 2.5 or greater as described by C. G. Swain and C. B. Scott in J. Am. Chem. Soc., Vol. 75, p. 141 (1953) which is incorporated herein by reference.

DETAILED DESCRIPTION OF THE INVENTION

The catalysts employed in the present invention are prepared by simply mixing in the desired proportions and stirring to insure intimate contact, the phosphine or arsine compound with the acid or salt of an acid having a weak-nucleophilic anion. The contact can be conducted at temperatures of from about 0° C. to about 100° C., preferably from about 20° C. to about 60° C. for a time sufficient to complete any reaction which occurs. The time depends upon the temperature, but usually from about 1 to about 120, preferably from about 5 to about 60 minutes is sufficient.

The components from which the catalysts are prepared are mixed in proportions which provide from about 0.6 to about 1.4, preferably from about 0.75 to about 1.35, most preferably form about 0.95 to about 1.2, moles of acid (b) per mole of phosphine or arsine compound (a); or the molar ratio of inorganic acid or metal salt of such acid which has a weak-nucleophilic anion (b) to an adduct of an acid having a relatively strong-nucleophilic anion and an organic phosphine or arsine (b) is from about 0.6 to about 1.4, preferably from about 0.75 to about 1.35, most preferably from about 0.95 to about 1.2.

The catalyst is employed in amounts sufficient to catalyze the reaction between components (A) and (B) when heated to a temperature of at least about 75° C. In most instances, the quantity of catalyst is from about 0.05 to about 100, suitably from about 0.1 to about 50, more suitably from about 0.5 to about 20, most suitably from about 1 to about 10 millimoles of catalyst per epoxide equivalent.

Suitable phosphine or arsine compounds which can be employed to prepare the catalysts include those represented by the following formulas III or IV

Formula III.

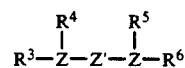
Formula IV.

wherein each R, $R^1$, $R^2$, $R^3$, $R^4$, $R^5$ and $R^6$ is independently a hydrocarbyl or hydrocarbyloxy group having suitably from 1 to about 18, more suitably from 1 to about 9, most suitably from 1 to about 6, carbon atoms or two of such R, $R^1$, or $R^2$ groups or $R^3$ and $R^4$ or $R^5$ and $R^6$ groups can combine to form a heterocyclic ring; and Z is P or As. Particularly suitable such compounds include, for example, triphenylphosphine, trimethylphosphine, tripropylphosphine, tributyl phsophine, tripentylphosphine, triheptylphosphine, trioctylphosphine, trinonylphosphine, tridecylphosphine, triundecyphosphine, tridodecylphosphine, bis(diphenylphosphino)-methane, 1,2-bis(diphenylphosphino)-ethane, 1,3-bis(diphenylphosphino)-propane, 1,2-bis(-dimethylphosphino)-ethane, 1,3-bis(dimethylphosphino)-propane, any combination thereof and the like.

Particularly suitable inorganic acids having a weak nucleophilic anion include, for example, fluoboric acid, fluoarsenic acid, fluoantimonic acid, fluphosphoric acid, chloroboric acid, chloroarsenic acid, chloroantimonic acid, chlorophosphoric acid, perchloric acid, chloric acid, bromic acid, iodic acid and any combination thereof and the like. Most particularly suitable such acid is fluoboric acid.

Fluoboric acid is sometimes referred to as fluoroboric acid or hydrogen tetrafluoroborate. Any of these expressions refer to the chemical represented by the formula, $HBF_4$.

Suitable metal salts of inorganic acids free from any organic substituents and having a weak nucleophilic anion include, for example those metals of Groups I and II of the Periodic Table of the Elements published by Sargent-Welch Scientific Company as catalog number S-18806. Particularly such salts include, for example, the sodium, potassium, lithium, calcium, barium, magnesium and silver salts of such inorganic acids.

Suitable compounds having an average of more than one epoxide group per molecule which can be employed herein include, epoxy resins such as, for example, the glycidyl ethers of polyhydric phenols such as dihydroxy phenols, biphenols, bisphenols, halogenated bisphenols, alkylated bisphenols, trisphenols, phenol-aldehyde novolac resins, substituted phenol-aldehyde novolac resins, phenol-hydrocarbon resins, substituted phenol-hydrocarbon resins, any combination thereof and the like. Suitable such epoxy resins include, for example, those represented by the following formulas V-IX.

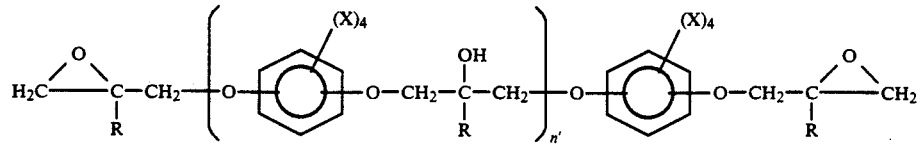
Formula V.

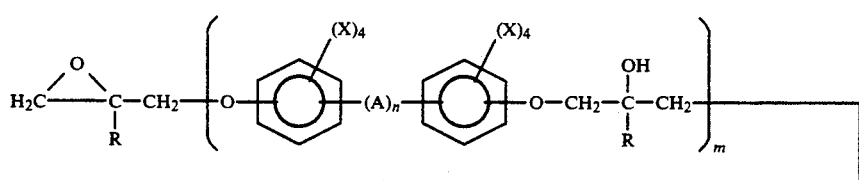

Formula VI.

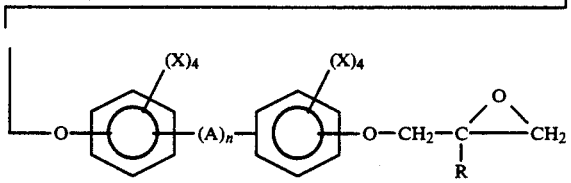

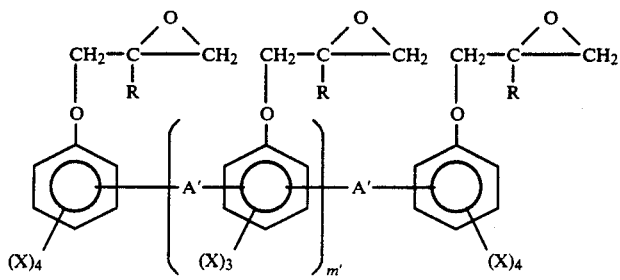

Formula VII.

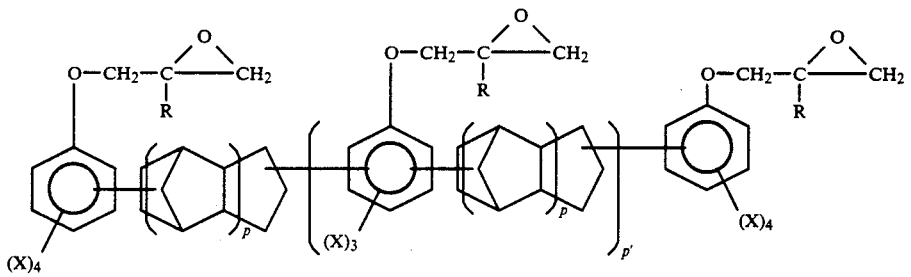

Formula VIII.

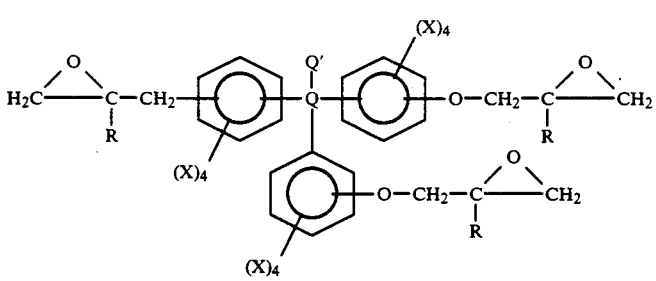

Formula IX.

wherein each A is independently a divalent hydrocarbyl group having from 1 to about 9, preferably from 1 to about 4, carbon atoms, —O—, —S—, —S—S—, —SO—, —SO$_2$—, or —CO—; each A' is independently a divalent hydrocarbyl group having from 1 to about 9, preferably from 1 to about 4 carbon atoms; Q is a hydrocarbyl group having from 1 to about 10 carbon atoms; Q' is hydrogen, halogen, cyano or an alkyl group having from 1 to about 4 carbon atoms; each R is independently hydrogen, halogen, cyano or an alkyl group having from 1 to about 4 carbon atoms; each X is independently hydrogen, bromine, chlorine, or a hydrocarbyl or hydrocarbyloxy group having from 1 to about 9, preferably from 1 to about 4 carbon atoms; m has an average value from zero to about 12, preferably from about zero to about 9, most preferably from about 0.03 to about 3; m' has an average value from about 0.01 to about 8, preferably from about 0.2 to about 6, more preferably from about 0.5 to about 4; n has a value of zero or 1; n' has an average value of from zero to about 12, preferably from zero to about 9, most preferably from about 0.03 to about 3; each p suitably has a value from zero to about 10, more suitably from zero to about 6, most suitably from about 1 to about 3; and each p' suitably has a value from zero to about 8, more suitably from about 1 to about 6, most suitably from about 2 to about 4. Also suitable are the oligomers of the epoxy resin represented by formula IX.

The term hydrocarbyl as employed herein means any aliphatic, cycloaliphatic, aromatic, aryl substituted aliphatic or cycloaliphatic, or aliphatic or cycloaliphatic substituted aromatic groups. The aliphatic groups can be saturated or unsaturated. Likewise, the term hydrocarbyloxy means a hydrocarbyl group having an oxygen linkage between it and the carbon atom to which it is attached.

Particularly suitable such epoxy resins include, for example, the diglycidyl ethers of resorcinol, catechol, hydroquinone, biphenol, bisphenol A, bisphenol F, bisphenol K, tetrabromobisphenol A, phenol-formaldehyde novolac resins, alkyl substituted phenol-formaldehyde resins, phenol-hydroxybenzaldehyde resins, cresol-hydroxybenzaldehyde resins, dicyclopentadiene-phenol resins, dicyclopentadiene-substituted phenol resins tetramethylbiphenol, tetramethyl-tetrabromobiphenol, tetramethyltribromobiphenol, tetrachlorobisphenol A, any combination thereof and the like.

Also suitable as the epoxide compound which can be employed in the present invention include those partially advanced epoxy resins disclosed by Bertram et al. in U.S. Pat. No. 4,594,291 which is incorporated herein by reference.

Also suitable as the epoxide compound are the glycidyl ethers of compounds having an average of more than one aliphatic hydroxyl group per molecule such as, for example, aliphatic diols, polyether diols, polyether triols, polyether tetrols, any combination thereof and the like. Also suitable are the alkylene oxide adducts of compounds containing an average of more than one aromatic hydroxyl group per molecule such as, for example, the ethylene oxide, propylene oxide, or butylene oxide adducts of dihydroxy phenols, biphenols, bisphenols, halogenated bisphenols, alkylated bisphenols, trisphenols, phenol-aldehyde novolac resins, halogenated phenol-aldehyde novolac resins, alkylated phenol-aldehyde novolac resins, hydrocarbon-phenol resins, hydrocarbon-halogenated phenol resins, or hydrocarbon-alkylated phenol resins, or any combination thereof and the like.

Suitable aromatic hydroxyl containing compounds which can be employed herein include, for example, compounds having an average of more than one phenolic hydroxyl group per molecule. Suitable such compounds include, for example, dihydroxy phenols, biphenols, bisphenols, halogenated bisphenols, alkylated bisphenols, trisphenols, phenol-aldehyde resins, halogenated phenol-aldehyde novolac resins, alkylated phenol-aldehyde novolac resins, phenol-hydroxybenzaldehyde resins, alkylated phenol-hydroxybenzaldehyde resins, hydrocarbon-phenol resins, hydrocarbon-halogenated phenol resins, hydrocarbon-alkylated phenol resins, any combination thereof and the like. Particularly suitable aromatic hydroxyl containing compounds include, for example, those represented by the following formulas X-XIII

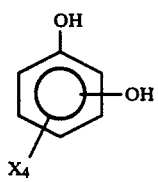

Formula X.

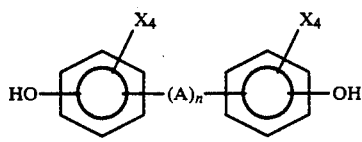

Formula XI.

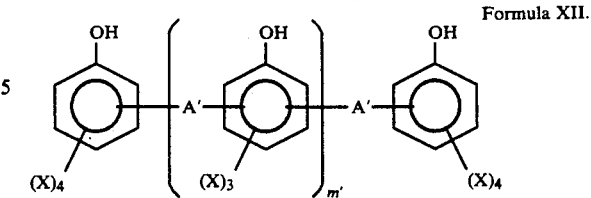

Formula XII.

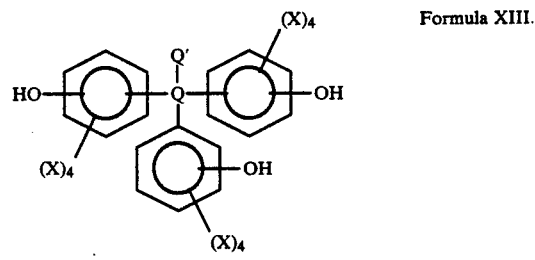

Formula XIII.

wherein A, A', Q, Q' X, n and m are as defined above in formulas V-IX. Particularly suitable aromatic hydroxyl-containing materials include, for example, biphenol, bisphenol A, bisphenol K, tetrabromobisphenol A, tetrabromobisphenol K, resorcinol, phenol-aldehyde novolac resins, cresol-aldehyde novolac resins, phenol-hydroxybenzaldehyde resins, cresol-hydroxybenzaldehyde resins, tetramethylbiphenol, tetramethyltribromobiphenol, tetramethyltetrabromobiphenol, tetrachorobisphenol A, any combination thereof and the like. Also suitable are the oligomers of the multifunctional phenolic compounds represented by the formula XIII.

These and other suitable aromatic hydroxyl-containing compounds are disclosed in U.S. Pat. No. 4,594,291 issued Jun. 10, 1986 to Bertram et al which is incorporated herein by reference in its entirety.

The aromatic hydroxyl-containing compounds are employed in amounts which provide a ratio of aromatic hydroxyl groups to epoxy groups suitably from about 0.05:1 to about 20:1, more suitably from about 0.1:1 to about 10:1, most suitably from about 0.2:1 to about 5:1.

The precatalyzed compositions of the present invention can contain, if desired, pigments, fillers, dyes, diluents, solvents, stabilizers, epoxy resin curing agents, any combination thereof and the like.

Suitable stabilizer materials and curing agents which can be employed herein include, for example, those disclosed in the aforementioned U.S. Pat. No. 4,594,291 by Bertram et al which is incorporated herein by reference in its entirety.

Particular suitable solvents or diluents include, for example, aliphatic and aromatic hydrocarbons, alcohols, ketones, glycol ethers, glycol esters, combinations thereof and the like. Particularly suitable solvents or diluents include, for example, ethylene glycol monobutyl ether (2-butoxyethanol), diethyleneglycol monopropyl ether, diethylene glycol monobutyl ether, diethylene glycol monohexyl ether monopropyl ether, propylene glycol monobutyl ether, propylene glycol tertiary butyl ether, propylene glycol isopropyl ether, dipropylene glycol monobutyl ether, ethylene glycol phenyl ether, propylene glycol phenyl ether, toluene, xylene, propylene glycol methyl acetate ether, any combination thereof and the like.

The compositions of the present invention are useful in the preparation of formulations for use in the preparation of electrical and structural laminates and composites, coatings, castings, moldings, encapsulants and the like. They can be employed in the conventional methods or the newer reaction transfer molding (RTM) and reaction injection molding (RIM) techniques.

The following examples are illustrative of the invention but are not to be construed as to limiting the scope thereof in any manner.

EXAMPLE 1

A 30% solution of a 1:1 molar ratio of triphenylphosphine/fluoroboric acid complex is made by adding 2.98 g (0.01906 mol) of a 56.1% solution of fluoroboric acid in water to a solution of 5.00 g (0.01906 mol) of triphenylphosphine in 14.26 g of tetrahydrofuran. The mixture is stirred at 25° C. for 5 minutes to insure intimate mixing. The concentration of the aqueous fluoroboric acid is determined by potentiometric titration to the first inflection point with 0.100N potassium hydroxide in methanol. An MCI GT-05 Automatic Titrator and a combination silver/silver chloride electrode (Curtain Matheson Scientific No. 201-947) are used to measure the pH changes during the course of the titration.

EXAMPLE 2

A 30% solution of a 1.00:1.10 molar ratio of triphenylphosphine/fluoroboric acid complex is made by adding 3.28 g (0.0210 mol) of 56.1% solution of fluoroboric acid in water to a solution of 5.00 g (0.01906 mol) of triphenylphosphine in 14.52 g of tetrahydrofuran. The mixture is stirred at 25° C. for 5 minutes to insure intimate mixing. The concentration of the aqueous fluoroboric acid is determined as in Example 1.

EXAMPLE 3

A 30% solution of a 1:1 molar ratio of tributylphosphine/fluoroboric acid complex is made by adding 1.93 g (0.01236 mol) of a 56.1% solution of fluoroboric acid in water to a solution of 2.50 g (0.01236 mol) of triphenylphosphine in 7.52 g of tetrahydrofuran. The mixture is stirred at 25° C. for 5 minutes to insure intimate mixing. The concentration of the aqueous fluoroboric acid is determined as in Example 1.

EXAMPLE 4

A 30% solution of a 1:1 molar ratio of 1,3-bis(diphenylphosphino)propane/fluoroboric acid complex is made by adding 1.52 g (0.00972 mol) of a 56.1% solution of fluoroboric acid in water to a solution of 2.00 g (0.00484 mol) of 1,3-bis(diphenylphosphino)propane in 5.99 g of tetrahydrofuran. The mixture is stirred at 25° C. for 5 minutes to insure intimate mixing. The concentration of the aqueous fluoroboric acid is determined as in Example 1.

EXAMPLE 5

1.71 g (18 mmol catalyst/mol epoxide) of the 30% catalyst solution described in Example 1 is added to 30.0 g of a 1:1 molar mixture of a diglycidyl ether of bisphenol A having an epoxide equivalent weight (EEW) of 181.5 and bisphenol A in 1-methoxy-2-acetoxypropane solvent (80% solids). This catalyzed mixture is placed in a 50° C. oven and the 25° C. viscosity is monitored after 0, 0.3, 1, 7, and 14 days. The results are provided in Table I.

EXAMPLE 6

1.75 g (18 mmol catalyst/mol epoxide) of the 30% catalyst solution described in Example 2 is added to 30.0 g of 1:1 molar mixture of a diglycidyl ether of bisphenol A having an epoxide equivalent weight (EEW) of 181.5 and bisphenol A in 1-methoxy-2-acetoxypropane solvent (80% solids). This catalyzed mixture is placed in a 50° C. oven and the 25° C. viscosity is monitored after 0, 1, 7, and 14 days. The results are provided in Table I.

EXAMPLE 7

1.41 g (18 mmol catalyst/mol epoxide) of the 30% catalyst solution described in Example 3 is added to 30.0 g of 1:1 molar mixture of a diglycidyl ether of bisphenol A having an epoxide equivalent weight (EEW) of 181.5 and bisphenol A in 1-methoxy-2-acetoxypropane solvent (80% solids). This catalyzed mixture is placed in a 50° C. oven and the 25° C. viscosity is monitored after 0, 0.3, 1, 7, and 14 days. The results are provided in Table I.

EXAMPLE 8

1.43 g (18 mmol catalyst/mol epoxide) of the 30% catalyst solution described in Example 4 is added to 30.0 g of 1:1 molar mixture of a diglycidyl ether of bisphenol A having an epoxide equivalent weight (EEW) of 181.5 and bisphenol A in 1-methoxy-2-acetoxypropane solvent (80% solids). This catalyzed mixture is placed in a 50° C. oven and the 25° C. viscosity is monitored after 0, 1, 7, and 14 days. The results are provided in Table I.

TABLE I

Time Versus Viscosity Data

| Ex. No. | Catalyst | Viscosity; after the indicated days centipoise (Pa · s) | | | | |
|---|---|---|---|---|---|---|
| | | 0 | 0.31 | 1 | 7 | 14 |
| 5 | $Ph_3P$—$HBF_4$ | 678 (0.678) | 720 (0.720) | 826 (0.826) | 3,180 (3.18) | 26,000 (26.0) |
| 6 | $Ph_3P$—$HBF_4$ | 704 (0.704) | — | 714 (0.714) | 877 (0.877) | 2,500 (2.500) |
| 7 | $nBu_3P$—$HBF_4$ | 611 (0.611) | 619 (0.619) | 631 (0.631) | 729 (0.729) | 857 (0.857) |
| 8 | 1,3-$(Ph_2P)_2$propane-$HBF_4$ | 749 (0.749) | — | 849 (0.849) | 1,380 (1.380) | 2,210 (2.210) |

EXAMPLES 9–12

Each of the initiators described in Examples 1–4 are used to promote the polymerization of a 1:1 molar mixture (295.5 g/equiv. epoxide) of the diglycidyl ether of bisphenol A having an epoxide equivalent weight (EEW) of 181.5 and bisphenol A. The amount of each catalyst added to 10.00 g of the epoxy/bisphenol mixture is arbitrarily set at 18 equiv. of initiator/epoxide equiv. The equivalent weight of each initiator and the weight of 18 equiv. of the 30% initiator solutions in tetrahydrofuran (THF) are provided in Table II. Also provided in Table II are the glass transition temperatures of the cured samples as determined by differential scanning calorimetry. All the samples are cured at 200° C. for 3.5 hours.

TABLE II

| | | Cured Resin Data | | |
|---|---|---|---|---|
| Example Number | Initiator | Initiator Equiv. Weight (g/equiv.) | g Initiator/10.00 g epoxy-bisphenol A | Glass Trans. Temp. (°C.) |
| 9 | $Ph_3P$—$HFB_4$ (Ex. 1) | 350.1 | 0.711 | 93 |
| 10 | $Ph_3P$—1.1 $HBF_4$ (Ex. 2) | 358.8 | 0.729 | 95 |
| 11 | $Bu_3P$—$HBF_4$ (Ex. 3) | 290.1 | 0.589 | 98 |
| 12 | 1,3-$(Ph_2P)_2$propane-$HBF_4$ (Ex. 4) | 250.1 | 0.508 | 100 |

What is claimed is:

1. A composition comprising (A) at least one compound containing an average of more than one epoxide group per molecule; and (B) at least one of (1) the product resulting from contacting (a) at least one organic arsine or organic phosphine compound, said organic phosphine compound being represented by the following formula III

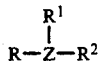

Formula III.

wherein each R, $R^1$ and $R^2$ is independently a hydrocarbyl group having from 1 to about 18 carbon atoms or two of said R, $R^1$, or $R^2$ groups can combine to form a heterocyclic ring, and Z is P, with (b) an inorganic acid having a weak-nucleophilic anion or a combination of said acids; or (2) the product resulting from contacting (a) at least one adduct of an acid having a relatively strong-nucleophilic anion and an organic phosphine or arsine compound with (b) an inorganic acid or metal salt of an inorganic acid, said acid having a weak-nucleophilic anion or a combination of said acids or metal salts; wherein (i) components (a) and (b) are contacted in quantities which permit the composition to satisfy the viscosity requirements of the composition after storage at 50° C. for 14 days; and (ii) the mixture of components (A), and (B), when dissolved in 20 to 40 percent by weight of a suitable solvent or solvent mixture, has a viscosity measured at 25° C. of 75% or less than the viscosity of a like composition except that the catalyst consists only of component (a), said viscosity being determined after storage for 14 days at 50° C.; and wherein component (B1a) is not triphenylphosphine when component (B1b) is tetrafluoroborate.

2. A composition of claim 1 wherein
   (i) in component (A), said epoxide groups are glycidyl ether groups;
   (ii) component (B-2-a) is an adduct of an acid having a relatively strong-nucleophilic anion and an organic phosphine; and
   (iii) the mixture of components (A), and (B), when dissolved in 20 to 40 percent by weight of a suitable solvent or solvent mixture, has a viscosity measured at 25° C. of 75% or less than the viscosity of a like composition except that the catalyst consists only of component (a), said viscosity being determined after storage for 14 days at 50° C.

3. A composition of claim 1 wherein component (B) is a product resulting from contacting (a) at least one organic phosphine with (b) an inorganic acid having a weak-nucleophilic anion or a combination of said acids; and the mixture of components (A), and (B), when dissolved in 20 to 40 percent by weight of a suitable solvent or solvent mixture, has a viscosity measured at 25° C. of 10% or less than the viscosity of a like composition except that the catalyst consists only of component (a), said viscosity being determined after storage for 14 days at 50° C.

4. A composition of claim 3 wherein

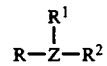

Formula III.

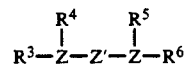

Formula IV.

component (b) is fluoboric acid, fluoarsenic acid, fluoantimonic acid, fluophosphoric acid, chloroboric acid, chloroarsenic acid, chloroantimonic acid, chlorophosphoric acid, perchloric acid, chloric acid, bromic acid, iodic acid, Group I or Group II metal salts of said acids, or any combination thereof.

5. A composition of claim 4 wherein component (b) is fluoboric acid, fluoantimonic acid, fluophosphoric acid, chloroboric acid, chloroarsenic acid, chloroantimonic acid, chlorophosphoric acid, perchloric acid, chloric acid, bromic acid, iodic acid, or any combination thereof.

6. A composition of claim 5 wherein said organic phosphine is triethylphosphine, or tributylphosphine, or any combination thereof; and component (b) is $HBF_4$.

7. A composition comprising (A) at least one compound containing an average of more than one epoxide group per molecule; (B) at least one compound containing an average of more than one aromatic hydroxyl group per molecule; and (C) at least one catalyst selected from the group consisting of (1) the product resulting from contacting (a) at least one organic phosphine or arsine with (b) an inorganic acid having a weak-nucleophilic anion or a combination of said acids; and (2) the product resulting from contacting (a) at least one adduct of an acid having a relatively strong-nucleophilic anion and an organic phosphine or arsine compound with (b) an inorganic acid or metal salt of an inorganic acid, said acid having a weak-nucleophilic anion or a combination of such acids or metal salts; wherein (i) components (a) and (b) are contacted in quantities which permit the composition to satisfy the viscosity requirements of the composition after storage at 50° C. for 14 days; (ii) components (A) and (B) are present in quantities which provide a ratio of aromatic hydroxyl groups to epoxide group of from about 0.05:1 to about 20:1; and (iii) a mixture of components (A), (B), and (C), when dissolved in 20 to 40 percent by weight of a suitable solvent or solvent mixture, has a viscosity measured at 25° C. of 75% or less than the viscosity of a like composition except that the catalyst consists only of component (a), said viscosity being determined after storage for 14 days at 50° C.

8. A composition of claim 7 wherein
   (i) in component (A), said epoxide groups are glycidyl ether groups;
   (ii) component (B) is a biphenol, bisphenol or a phenol- or substituted phenol-aldehyde novolac resin;
   (iii) component (C-1-a) is an organic phosphine;
   (iv) component (C-2-a) is an adduct of an acid having a relatively strong-nucleophilic anion and an organic phosphine; and
   (v) the mixture of components (A), (B) and (C), when dissolved in 20 to 40 percent by weight of a suitable solvent or solvent mixture, has a viscosity measured at 25° C. of 10% or less than the viscosity of a like composition except that the catalyst consists only of component (a), said viscosity being determined after storage for 14 days at 50° C.

9. A composition of claim 8 wherein component (C) is a product resulting from contacting (a) at least one organic phosphine with (b) an inorganic acid having a weak-nucleophilic anion or a combination of said acids; and the mixture of components (A), (B) and (C), when dissolved in 20 to 40 percent by weight of a suitable solvent or solvent mixture, has a viscosity measured at 25° C. of 1% or less than the viscosity of a like composition except that the catalyst consists only of component (a), said viscosity being determined after storage for 14 days at 50° C.

10. A composition of claim 9 wherein component (a) is an organic phosphine represented by the following formulas III or IV

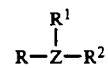
Formula III.

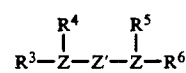
Formula IV.

wherein each R, $R^1$, $R^2$, $R^3$, $R^4$, $R^5$ and $R^6$ is independently a hydrocarbyl group having from 1 to about 18 carbon atoms or two of said R, $R^1$, or $R^2$ groups or $R^3$ and $R^4$ or $R^5$ and $R^6$ groups can combine to form a heterocyclic ring; and Z is P; Z' is a divalent hydrocarbyl group having from 1 to about 10 carbon atoms; and component (b) is fluoboric acid, fluoarsenic acid, fluoantimonic acid, fluophosphoric acid, chloroboric acid, chloroarsenic acid, chloroantimonic acid, chlorophosphoric acid, perchloric acid, chloric acid, bromic acid, iodic acid, Group I or Group II metal salts of said acids, or any combination thereof.

11. A composition of claim 10 wherein each R, $R^1$, $R^2$, $R^3$, $R^4$, $R^5$ and $R^6$ is independently a hydrocarbyl group having from 1 to about 9 carbon atoms; and component (b) is fluoboric acid, fluoantimonic acid, fluophosphoric acid, chloroboric acid, chloroarsenic acid, chloroantimonic acid, chlorophosphoric acid, perchloric acid, chloric acid, bromic acid, iodic acid, or any combination thereof.

12. A composition of claim 11 wherein said organic phosphine is triethylphosphine, tributylphosphine, or 1,3-bis(diphenylphosphino)propane, or any combination thereof; and component (b) is $HBF_4$.

* * * * *